(12) United States Patent
Cheon et al.

(10) Patent No.: US 10,899,708 B2
(45) Date of Patent: Jan. 26, 2021

(54) METHOD FOR PURIFYING N-SUBSTITUTED MALEIMIDE

(71) Applicant: LG CHEM, LTD., Seoul (KR)

(72) Inventors: Joo Young Cheon, Daejeon (KR); Jun Seon Choi, Daejeon (KR); Ji Yeon Kim, Daejeon (KR); Ki Hyuk Kang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/615,015

(22) PCT Filed: Aug. 29, 2018

(86) PCT No.: PCT/KR2018/010008
§ 371 (c)(1),
(2) Date: Nov. 19, 2019

(87) PCT Pub. No.: WO2019/124674
PCT Pub. Date: Jun. 27, 2019

(65) Prior Publication Data
US 2020/0207710 A1    Jul. 2, 2020

(30) Foreign Application Priority Data
Dec. 21, 2017   (KR) .......................... 10-2017-0177054

(51) Int. Cl.
*C07D 207/448*   (2006.01)

(52) U.S. Cl.
CPC ................................ *C07D 207/448* (2013.01)

(58) Field of Classification Search
CPC .................................................. C07D 207/448
See application file for complete search history.

(56) References Cited

U.S. PATENT DOCUMENTS

| | | | |
|---|---|---|---|
| 4,851,547 A | 7/1989 | Kita et al. | |
| 4,904,803 A | 2/1990 | Fujita et al. | |
| 5,136,052 A | 8/1992 | Van Gysel et al. | |
| 10,487,052 B2 * | 11/2019 | Cheon | C07D 207/448 |

FOREIGN PATENT DOCUMENTS

| | | |
|---|---|---|
| CN | 103664732 A | 3/2014 |
| EP | 0257831 A1 | 3/1988 |
| JP | H01216969 A | 8/1989 |
| JP | H06184103 A | 7/1994 |
| JP | H06345729 A | 12/1994 |
| JP | H075547 B2 | 1/1995 |
| JP | H0720932 B2 | 3/1995 |
| JP | H0774197 B2 | 8/1995 |
| JP | H0774198 B2 | 8/1995 |
| JP | 2669923 B2 | 10/1997 |
| JP | 2001302627 A | 10/2001 |
| JP | 2003055342 A | 2/2003 |
| KR | 20090069016 A | 6/2009 |
| WO | WO2018124453 A1 | 7/2018 |

OTHER PUBLICATIONS

Kamiya, et al., "Zirconium Phosphate with a High Surface Area as a Water-Tolerant Solid Acid," Catalyst Letters, 2004, vol. 94 (1-2), pp. 45-47.
Search Report dated Dec. 4, 2018 for PCT Application No. PCT/KR2018/010008.

* cited by examiner

*Primary Examiner* — Golam M Shameem

(57) ABSTRACT

The present invention relates to a method for purifying N-substituted maleimide. More specifically, the present invention, without performing a water washing process, enables to remove organic-acid-impurities which are difficult to remove through distillation because of having similar boiling points to the N-substituted maleimide compound by utilizing solubility of organic-acid-impurities in an organic solvent used in the preparing process of the maleimide compound, and thereby, without producing washing wastewater, ensuring removal efficiency of the organic-acid-impurities equal to or similar to an N-substituted maleimide compound subjected to a water washing process.

12 Claims, No Drawings

METHOD FOR PURIFYING N-SUBSTITUTED MALEIMIDE

CROSS-REFERENCE TO RELATED APPLICATIONS

This present application is a U.S. National Stage of PCT/KR2018/010008, filed Aug. 29, 2018 which claims the benefit of Korean Patent Application No. 10-2017-0177054, filed Dec. 21, 2017, all of which is incorporated herein in its entirety by reference.

TECHNICAL FIELD

The present invention relates to a method for purifying N-substituted maleimide.

BACKGROUND ART

A maleimide compound is a useful compound as a raw material for a resin material, pharmaceutical and agricultural chemicals, etc., and particularly, widely used as one of copolymerization components for improving heat resistance of a styrene-based resin (for example, an ABS resin, an AS resin, an AB resin, an ACS resin, an AES resin, an AAS resin, etc.), a polyvinyl chloride resin, a poly methyl methacrylate resin, a phenol resin, etc. Among them, N-phenyl maleimide (hereinafter, also referred to as PMI.) is particularly widely used because of having excellent reactivity and heat resistance.

As methods for preparing a maleimide compound, there are many conventionally known methods, for example, 1) a method of obtaining a maleimide compound by a dehydration reaction of maleic anhydride (hereinafter, also referred to as MAH.) and primary amines in one step, 2) a method of obtaining a maleimide compound by a dehydration ring-closure imidization reaction of maleamic acids, which are produced from maleic anhydride and primary amines, 3) a method of obtaining a maleimide compound by a ring-closure imidization reaction of corresponding maleamic acid monoesters, etc.

Among these methods, the method 1) of obtaining a maleimide compound from maleic anhydride and primary amines in one step has a problem in that productivity is inferior because yield is still low; the method 3) of obtaining a maleimide compound from maleamic acid monoesters has a problem in that an alcohol, which is produced by a ring-closure imidization reaction, is left and mixed in a product. Thus, the method 2) of obtaining a maleimide compound by a dehydration ring-closure imidization reaction of maleamic acids is commercially and generally carried out.

On the other hand, when N-phenyl maleimide is prepared, primary amines are anilines (hereinafter, also referred to as ANL.), and maleamic acids are N-phenyl maleamic acids (hereinafter, also referred to as PMA.).

The maleimide compound prepared is subjected to a purification process to remove impurities produced during a preparing process of the maleimide compound, and then, a high-purity maleimide compound can be obtained.

However, some organic acids having similar boiling points to the maleimide compound are difficult to remove through simple distillation, and therefore, a water washing process using water is necessarily required. However, since a large amount of wastewater containing impurities is produced in the water washing process using the water, there is a problem of requiring high costs for installing an additional wastewater treatment facility and maintaining thereof.

Accordingly, inventors of the present invention have conducted a study to solve the above problem and found that when the organic-acid-impurities were removed through simple filtration utilizing solubility of the organic-acid-impurities in the organic solvent used in the preparing process of the maleimide compound, removal efficiency of the organic-acid-impurities equal to or similar to a maleimide compound subjected to a water washing process was ensured without producing washing wastewater, and thus the present invention has been accomplished.

PRIOR ART DOCUMENT (Patent Document 1) JP 2001-302627 A (2001 Oct. 31)

DISCLOSURE OF THE INVENTION

Technical Problem

An aspect of the present invention provides a method for purifying N-substituted maleimide compound, the method being capable of removing organic-acid-impurities, which are difficult to remove through distillation because of having similar boiling points to an N-substituted maleimide compound, by utilizing solubility of organic-acid-impurities in an organic solvent used in a preparing process of a maleimide compound.

Another aspect of the present invention provides a method for purifying an N-substituted maleimide compound, the method being capable of ensuring removal efficiency of organic-acid-impurities equal to or similar to an N-substituted maleimide compound subjected to a water washing process while not performing a water washing process and not producing washing wastewater.

Another aspect of the present invention provides a method for purifying an N-substituted maleimide compound, the method being minimizing catalyst loss by adopting a zirconium (IV) hydrogen phosphate solid-acid-catalyst as a catalyst in a synthesis process for N-substituted maleimide, thereby not requiring catalyst supplement in a synthesis reaction. In addition, the method is also capable of separating the catalyst only through simple filtration in a purification process for N-substituted maleimide, thereby providing a simplified purification process for N-substituted maleimide.

Technical Solution

To solve the above-described problems according to the aspects of the present invention, there is provided a method for purifying N-substituted maleimide, including:

1) a step of preparing an N-substituted maleimide solution produced by reacting with maleic anhydride and a primary amine in the presence of an organic solvent and a catalyst; and 2) a step of cooling the N-substituted maleimide solution to 50° C. to 60° C. to precipitate a solidified organic acid, removing a solidified organic acid by filtering.

Advantageous Effects

The method for purifying the N-substituted maleimide according to the present invention is capable of removing organic-acid-impurities which are difficult to remove through distillation because of having similar boiling points to an N-substituted maleimide compound without performing a water washing process.

In addition, the present invention is capable of ensuring removal efficiency of organic-acid-impurities equal to or similar to an N-substituted maleimide compound subjected to a water washing process while not performing a water washing process and not producing washing wastewater.

In addition, the present invention is capable of minimizing catalyst loss by adopting a zirconium(IV) hydrogen phosphate solid-acid-catalyst as a catalyst in a synthesis process for N-substituted maleimide, thereby not requiring catalyst supplement in a synthesis reaction, and thus is capable of separating the catalyst only through simple filtration in a purification process for N-substituted maleimide.

MODE FOR CARRYING OUT THE INVENTION

Hereinafter, the present invention will be described in more detail to allow for a clearer understanding of the present invention.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

The present invention provides a method for purifying N-substituted maleimide, including:

1) a step of preparing an N-substituted maleimide solution produced by reacting with maleic anhydride and a primary amine in the presence of an organic solvent and a catalyst; and 2) a step of cooling the N-substituted maleimide solution to 50° C. to 60° C. to precipitate a solidified organic acid, removing the solidified organic acid by filtering.

Hereinafter, the method for purifying N-substituted maleimide of the present invention will be described in detail.

Step 1)

The step 1) according to one example of the present invention is a step for preparing an N-substituted maleimide solution to be purified, the step being characterized by synthesizing the N-substituted maleimide by reacting with maleic anhydride and a primary amine in the presence of an organic solvent and a catalyst.

The N-substituted maleimide solution is a solution produced by the N-substituted maleimide synthesis reaction in step 1), and the solution may contain the organic solvent (non-polar organic solvent) used in the synthesis reaction, the N-substituted maleimide product, and impurities such as unreacted products and by-products in addition to the catalyst used for preparing the N-substituted maleimide.

On the other hand, the N-substituted maleimide contained in the N-substituted maleimide solution may be 20 to 40 wt %, preferably 30 wt % to 35 wt %, based on the weight of the N-substituted maleimide solution.

As methods for preparing the N-substituted maleimide compound, there are several methods, for example, 1) a method of obtaining the N-substituted maleimide compound by a dehydration reaction of maleic anhydride and a primary amine in one step, 2) a method of obtaining the N-substituted maleimide compound by a dehydration ring-closure imidization reaction of maleamic acid, which is produced from maleic anhydride and a primary amine, 3) a method of obtaining the N-substituted maleimide compound by a ring-closure imidization reaction of a corresponding maleamic acid monoester, etc.

However, the method 1) of obtaining the N-substituted maleimide compound from maleic anhydride and a primary amine in one step has a problem in that productivity is inferior because yield is still low; the method 3) of obtaining the N-substituted maleimide compound from a maleamic acid monoester has a problem in that an alcohol, which is produced by a ring-closure imidization reaction, is left and mixed in the product. Thus, the method for preparing the N-substituted maleimide compound of the present invention will be described in detail with reference to an embodiment for the method 2) of synthesizing the N-substituted maleimide compound by a dehydration ring-closure imidization reaction of a maleamic acid.

The N-substituted maleimide of the present invention can be synthesized by the method of: as a primary step, carrying out an acylation reaction on which maleic anhydride and a primary amine are heated to obtain N-substituted maleamic acid as a reaction intermediate; and as a secondary step, carrying out a dehydration ring-closure imidization reaction on the N-substituted maleamic acid on the catalyst surface.

Furthermore, in the primary step of obtaining the N-substituted maleamic acid from the maleic anhydride and the primary amine, the maleic anhydride or the primary amine may be used as it is, but it is preferable to be used in a solution form dissolved in the organic solvent. On the other hand, when the maleic anhydride or the primary amine is used in the solution form dissolved in the organic solvent, the following step of carrying out the dehydration ring-closure imidization reaction on the N-substituted maleamic acid can be carried out directly in the solution (organic solvent).

The organic solvent should be insoluble or immiscible in water, and inert to the reaction or nonparticipation in the reaction, so that water produced by the dehydration ring-closure imidization reaction on the N-substituted maleamic acid is discharged out of the system through azeotropic distillation.

In addition, for the smooth progress of the reaction, the organic solvent having a boiling point of at least 50° C. or more is appropriate, and for the stability of the N-substituted maleimide product, the organic solvent having a boiling point of less than 170° C. is appropriate. Examples of the suitable organic solvent include benzene, toluene, xylene, o-xylene, ethylbenzene, isopropylbenzene, cumene, mesitylene, tert-butylbenzene, pseudocumene, trimethylhexane, octane, tetrachloroethane, nonane, chlorobenzene, ethylcyclohexane, m-dichlorobenzene, sec-butylbenzene, p-dichlorobenzene, decane, p-cymene, o-dichlorobenzene, butylbenzene, decahydronaphthalene, tetrahydronaphthalene, dodecane, naphthalene, cyclohexylbenzene, etc., and the organic solvent may be used alone or in the form of a mixture of two or more.

The primary amine of the present invention may employ one selected from the primary amines containing saturated or unsaturated alkylamines having 1 to 20 carbon atoms, cycloalkylamines having 5 to 20 carbon atoms, cycloalkylamines having 6 to 20 carbon atoms, or aromatic alkylamines having 6 to 20 carbon atoms. More specifically, the primary amine may employ at least one selected from the group consisting of methylamine, ethylamine, n-propylamine, isopropylamine, n-butylamine, sec-butylamine, isobutylamine, tert-butylamine, n-hexylamine, n-octylamine, n-decylamine, n-dodecylamine, cyclohexylamine, or aniline, and the aniline may be used as a primary amine to synthesize N-phenyl maleimide.

In the present invention, a preferable amount of the maleic anhydride to be used is 1.0 to 1.3 molar ratio with regard to the primary amine used in the synthesis of the N-substituted maleimides. When the maleic anhydride is used in an amount of less than 1.0 molar ratio, problems such as a yield decrease and a by-product increase occur, and when the maleic anhydride is used in an amount of 1.3 or more molar ratio, the unreacted maleic anhydride is excessively left after the synthesis of the N-substituted maleimide, and thus it is not economically preferable.

On the other hand, either a homogeneous liquid catalyst directly or a supported catalyst, in which a homogeneous active component is supported on the carrier, has been mostly employed for the catalyst used in the conventional N-substituted maleimide synthesis method. However, when the homogeneous liquid catalyst was used, the catalyst loss may occur in a separation process of the catalyst from the product through performing layer-separation by the polarity difference after completing the synthesis reaction, and when the supported catalyst was used, the active component loss may occur by water, which is a by-product produced in the synthesis process of the N-substituted maleimide, and thus a continuous supplement to the loss of the active component was necessary. In addition, since the supplement to the active component was also possible after the supported catalyst was separated and dried, it had a problem in that the supplement to the active component was not easy because of becoming the complicated process.

In the preparing step for the N-substituted maleimide according to the present invention, since the N-substituted maleimide is synthesized by employing a heterogeneous solid-acid-catalyst unlike the homogeneous liquid catalyst or supported catalyst used in the conventional preparing method, it is characterized by being able to solve the above-conventional problems. Meanwhile, in the present invention, the 'homogeneous' means that the reactant and catalyst, which are used in the N-substituted maleimide synthesis reaction, have the same phases, and the 'heterogeneous' means that the reactant and catalyst have the different phases.

More specifically, the heterogeneous solid-acid-catalyst used in the present invention is characterized by being zirconium(IV) hydrogen phosphate ($Zr(H_2PO_4)_2$).

The zirconium(IV) hydrogen phosphate is an acidic and inorganic cation-exchange material having a layered structure. The zirconium(IV) hydrogen phosphate has some characteristics of having high thermal and chemical stability, solid ion conductivity and resistance to ionizing radiation, and of introducing different sizes and different types of the molecules within their layers. In addition, the zirconium (IV) hydrogen phosphate may exist in various types having various interlayer spaces and crystal structures, and the most widely known zirconium (IV) hydrogen phosphate is an alpha form of $Zr(HPO_4)_2 \cdot H_2O$ and a gamma form of $Zr(PO_4)(H_2PO_4) \cdot 2H_2O$.

In a case of the present invention, the zirconium (IV) hydrogen phosphate employed as a solid-acid-catalyst is not a crystalline structure of the alpha type and gamma type, but amorphous zirconium (IV) hydrogen phosphate. Also, the hydration degree of the zirconium (IV) hydrogen phosphate may vary depending on the reaction conditions, and the zirconium (IV) hydrogen phosphate may be represented by formula 1 below.

$$Zr_x(H_aPO_b)_c \quad \text{[Formula 1]}$$

(In Formula 1, $0.5 \leq x \leq 1.5$, $0 \leq a \leq 8$, $0 \leq b \leq 8$, and $1 \leq c \leq 4$.)

As described above, the N-substituted maleimide synthesis method of the present invention can minimize the possibility of the catalyst loss by employing the heterogeneous solid-acid-catalyst having the different phase from the reactant in the N-substituted maleimide synthesis reaction. More particularly, by employing the zirconium (IV) hydrogen phosphate among the solid-acid-catalysts, it is characterized in that the synthesis yield of the N-substituted maleimide is high.

More specifically, since the catalyst of the present invention is the solid phase having the different phase from the reactant, the problems of the active component loss by water, which is a by-product produced in the synthesis process of the N-substituted maleimide; and the catalyst loss in the layer-separation process after completing the synthesis reaction do not occur. In addition, since zirconium (IV) hydrogen phosphate employed to the present invention is structurally very stable, the reactivity to water is low, and supplement and regeneration of the catalyst during the reaction are not necessary, and thus there is an effect in that the preparing process for the N-substituted maleimide is also simplified.

On the other hand, depending on the case, a metal-containing compound or a stabilizer may be allowed to coexist and react in the reaction system. The metal-containing compound to be used in the reaction is not particularly limited, but may be a metal oxide, an acetate, a malate, a succinate, a nitrate, a phosphate, chloride and a sulfate of at least one selected from the group consisting of zinc, chromium, palladium, cobalt, nickel, iron and aluminum. Among these, a zinc acetate is particularly effective. An amount of the metal-containing compound or the stabilizer to be used is 0.005 mol % to 0.5 mol %, preferably 0.01 mol % to 0.1 mol % as a metal, with regard to the maleic anhydride and/or the primary amine which are/is the raw materials/material.

In addition, examples of the stabilizer include methoxybenzoquinone, p-methoxyphenol, phenothiazine, hydroquinone, alkylated diphenyl amines, methylene blue, tert-butylcatechol, tert-butylhydroquinone, zinc dimethyldithiocarbamate, copper dimethyldithiocarbamate, copper dibutyldithiocarbamate, copper salicylate, thiodipropionic acid esters, mercaptobenzimidazole, triphenylphosphite, alkyl phenols, alkyl bisphenols, etc. The effect of these stabilizers is to enable the N-substituted maleimide produced through the dehydration ring-closure imidization reaction to exist stably without transmutation even under the high temperature of the imidization reaction. An amount of the stabilizer to be added is not particularly limited, but 0.001 mol % to 0.5 mol % may be used with regard to the maleic anhydride and/or the primary amine which are/is the raw materials/material. Such an added amount in the above range can sufficiently achieve the stabilizing effect and can avoid the problem in that the stabilizer is mixed into the product.

The reaction temperature of the N-substituted maleimide synthesis reaction in step 1) according to the present invention is generally 50° C. to 200° C., more specifically 100° C. to 140° C. is preferable. When the synthesis reaction temperature is lower than the above range, a problem of the yield decrease occurs, and when the synthesis reaction temperature is higher than the above range, because of the side reaction, a problem of the purity and yield decrease of the synthesized N-substituted maleimide occurs.

The reaction pressure according to the present invention is not particularly limited, and the pressure may be selected from a wide range among the depressurized pressure, atmospheric pressure and pressurized pressure. In addition, the reaction time may be varied according to the conditions, such as a kind of the solvent, an added amount of the raw material, an amount of the catalyst and the reaction temperature, but is generally about 1 hour to 16 hours, more preferably 1 hour to 10 hours.

Under the above reaction conditions, the dehydration ring-closure imidization reaction of the N-substituted maleamic acid proceeds efficiently, and thereby obtaining the N-substituted maleimide efficiently.

The N-substituted maleimide prepared through the above-mentioned method may include at least one selected from the group consisting of: N-alkyl maleimide such as N-methyl maleimide, N-ethyl maleimide, N-hexyl maleimide, N-octyl maleimide, or N-dodecyl maleimide; N-benzyl maleimide; N-cycloalkyl maleimide such as N-cyclohexyl maleimide; N-phenyl maleimide; or N-substituted phenyl maleimide, in which a phenyl group is substituted with a nitro group, an alkoxy group, an alkyl group, a carboxyl group, a hydroxyl group, or a halogen group, such as N-nitrophenyl maleimide, N-methoxyphenyl maleimide, N-methylphenyl maleimide, N-carboxyphenyl maleimide, N-hydroxyphenyl maleimide, N-chlorophenyl maleimide, N-dimethylphenyl maleimide, N-dichlorophenyl maleimide, N-bromophenyl maleimide, N-dibromophenyl maleimide, N-trichlorophenyl maleimide, or N-tribromophenyl maleimide.

Step 2)

The step 2) according to one embodiment of the present invention is characterized by cooling the N-substituted maleimide solution prepared in step 1) to precipitate solidified organic acid impurities, removing the solidified organic acid impurities by filtering.

An object of the present invention is to, by utilizing the solubility of organic-acid-impurities in the organic solvent, remove organic-acid-impurities which are difficult to remove through distillation because of having similar boiling points to the N-substituted maleimide compound without performing a water washing process, and thus, a cooling process of the N-substituted maleimide solution is essential after the N-substituted maleimide synthesis reaction.

Generally, the organic-acid-impurities dissolve well in water or a polar solvent, but the solubilities of the organic-acid-impurities are very low in the non-polar organic solvent used in the N-substituted maleimide synthesis reaction. Therefore, when the temperature of the solution is high in the synthesis reaction process, the organic-acid-impurities are dissolved in the non-polar organic solvent, but when the temperature of the solution is lowered, the organic-acid-impurities are precipitated into a solid due to the low solubilities.

More specifically, the method for purifying the N-substituted maleimide according to the present invention is characterized by cooling the N-substituted maleimide solution to 50° C. to 60° C., more specifically 50° C. to 55° C., to precipitate the organic-acid-impurities into a solid.

When the temperature is lower than the above range, some of the N-substituted maleimide is precipitated in the process of removing the impurities, so that the loss of the N-substituted maleimide may occur. When the temperature is higher than the above range, an effect of removing the impurities is low since the organic-acid-impurities have the high solubilities in the organic solvent used for the present invention, so that it may be difficult to ensure the high-purity N-substituted maleimide.

On the other hand, the organic-acid-impurities to be removed by utilizing the solubility difference in the organic solvent according to the above temperature of the present invention, are characterized by including one or more selected from the group consisting of fumaric acid (FA), maleic acid (MA), N-phenyl maleamic acid (PMA), N-phenyl maleimide (PMI), N-(2,5-dioxo-1-phenyl-3-pyrrolidinyl)-N-phenyl maleamic acid) (PPMA), N-(2,5-dioxo-1-phenyl-3-pyrrolidinyl)-N-phenyl fumaranilic acid) (PPFA) and 2-anilino-N-phenyl succinimide (APSI).

More preferably, the present invention is more effective for removing the organic acid which is difficult to remove through distillation process since the organic acid has the most similar boiling point to the N-substituted maleimide. The boiling point difference between the organic acid and the N-substituted maleimide, that is, 'the boiling point of the N-substituted maleimide (° C.)—the boiling point of the organic acid (° C.)' may be −30° C. to 40° C., more specifically −20° C. to 40° C.

According to one example of the present invention, the fumaric acid (FA) cannot be removed through the distillation process in which impurities are removed by utilizing the differences of the boiling points since the boiling point of the N-substituted maleimide in the present invention is about 277° C. based on 570 mmHg, which is very similar to that of the fumaric acid (FA) having the boiling point of about 290° C. based on 570 mmHg, so that the fumaric acid (FA) is further condensed, thereby deteriorating the quality of the N-substituted maleimide.

Furthermore, when the water washing process using water is performed in order to remove the fumaric acid (FA), a large amount of wastewater containing the impurities is produced, and thus there is a problem in that it requires an additional wastewater treatment facility and costs for maintaining the same.

Accordingly, the present invention provides to a method for purifying the N-substituted maleimide, wherein the method is capable of removing the organic-acid-impurities, which are difficult to remove through the distillation because of having similar boiling points to the N-substituted maleimide compound, without performing the water washing process since the organic-acid-impurities are removed by utilizing the solubility difference to the organic solvent used in the above described step 1), thereby ensuring the removal efficiency of the organic-acid-impurities equal to or similar to an N-substituted maleimide compound subjected to a water washing process without producing washing wastewater.

According to one example of the present invention, an amount of the organic acid (i.e., fumaric acid (FA)) contained in the N-substituted maleimide solution of step 1) may be 0.1 wt % to 5.0 wt %, more specifically 0.1 wt % to 3.0 wt %, and after carrying out step 2), an amount of the organic acid (i.e., fumaric acid (FA)) contained in the N-substituted maleimide solution may be 0.03 wt % to 0.1 wt %, more specifically 0.03 wt % to 0.07 wt %.

The above amount indicates that the removal efficiency of the organic-acid-impurities is equal to or similar to an N-substituted maleimide compound subjected to a water washing process, thereby ensuring the high-purity N-substituted maleimide through the method of the present invention.

On the other hand, the method for purifying the N-substituted maleimide according to the present invention may further include a step of separating the catalyst from the N-substituted maleimide solution and the separation method for the catalyst is characterized by one method selected from a method for separating the catalyst with the organic acid together through the filtration in step 2), or a method for pre-separating the catalyst through the high-temperature filtration of 100° C. to 140° C., more specifically 100° C. to 110° C. prior to step 2).

The method for separating the catalyst in the N-substituted maleimide solution with the organic acid together has an advantage in that the process is simple in an aspect of unification of the filtration process, but when the N-substituted maleimide solution containing the catalyst is cooled, some of the catalyst may aggregate in the process of cooling/stirring. Therefore, the method for pre-separating the catalyst from the N-substituted maleimide solution in the high-temperature state prior to removal of the organic acid has an advantage in that the separated organic acid component can be prevented from re-introducing into the reactor with the catalyst together.

On the other hand, when the catalyst is a zirconium (IV) hydrogen phosphate ($Zr(H_2PO_4)_2$) solid-acid-catalyst, the catalyst can be separated by a simple process such as filtration, and there may be an advantage of regenerating the catalyst through a washing or firing process.

The present invention may further include a step of distilling the N-substituted maleimide solution from which the solidified organic acid is filtered out and removed in the above step 2), thereby obtaining a high-purity N-substituted maleimide product.

Example 1

20 mL of ethylbenzene as a solvent, 2.5 g of aniline, 2.9 g of maleic anhydride melted at 80° C., and 1.249 g of a zirconium (IV) hydrogen phosphate solid-acid-catalyst were added to a 100 mL reactor equipped with a stirrer, a thermometer, a water separator and a condenser, and the reactor was heated to 125° C. to synthesize N-phenyl maleimide. Water produced by a dehydration ring-closure reaction during the reaction process was removed from the reaction system together with ethylbenzene through azeotropic distillation. The synthesis reaction was carried out repeatedly for 4 hours while the ethylbenzene removed from the reaction system was re-introduced into the reaction system.

After completing the synthesis reaction, the zirconium (IV) hydrogen phosphate solid-acid-catalyst was separated previously through filtration from the solution containing the N-phenyl maleimide and ethylbenzene at the temperature of 110° C., and then the solution was cooled to 50° C. and stirred for 50 minutes. After the stirring, the solidified organic acid was removed through filtration to purify the N-phenyl maleimide.

Example 2

The N-phenyl maleimide was purified in the same manner as in Example 1 except that after the solidified organic acid in Example 1 was removed through filtration, the ethylbenzene was removed through distillation under the reduced pressure for 1 hour by raising the temperature to 80° C. under the reduced pressure of 10 mmHg, and then distillation was further carried out by using a thin film distiller having an inner diameter of 2 inches to increase the purity of the N-phenyl maleimide product under the conditions of the feed rate per minute of 6.7 to 9 g/min, the evaporation region temperature of 145° C., the condensation region temperature of 100° C., and the pressure of 3 mmHg.

Comparative Example 1

The N-phenyl maleimide was purified in the same manner as in Example 2 except that after completing the synthesis reaction in Example 2, the process for cooling the solution containing the N-phenyl maleimide and ethylbenzene to 50° C.; and filtering out the solidified organic acid was not carried out.

Comparative Example 2

The N-phenyl maleimide was purified in the same manner as in Example 1 except that the solution was cooled to 30° C. instead of 50° C. in Example 1.

Comparative Example 3

The N-phenyl maleimide was purified in the same manner as in Example 1 except that the solution was cooled to 80° C. instead of 50° C. in Example 1.

Reference Example 1

The N-phenyl maleimide was purified in the same manner as in Example 2 except that, instead of cooling the solution containing the N-phenyl maleimide and ethylbenzene, from which the solid-acid-catalyst was previously separated, to 50° C. in Example 2, after the solution was washed with water at a degree of 80° C. to 90° C., the ethylbenzene was removed through distillation under the reduced pressure, and thereafter the N-phenyl maleimide product was purified by using the thin film distiller.

Experimental Example

In the case of Example 1 and Comparative Examples 2 and 3, the organic acid was filtered out after carrying out precipitation, and the filtered N-phenyl maleimide solution was separated and diluted with a tetra-hydrofuran (THF) solution. Thereafter, the purity of the solution was measured by using a liquid chromatography (LC) analysis, and the results were shown in below Table 1.

In the case of Example 2, Comparative Example 1 and Reference Example 1, since the solution, which had subjected to the solvent removal process prior to the product purification process using the thin film distillation apparatus, was introduced into the thin film distillation apparatus, the solvent was not contained in the final N-phenyl maleimide (product) obtained before and after carrying out the product purification. Accordingly, the N-phenyl maleimide (melting point of 90° C.), which had been discharged from the thin film distillation apparatus, was coagulated at a room temperature (25° C.), and then the N-phenyl maleimide was separated and dissolved in a tetra-hydrofuran (THF) solution. Thereafter, the purity of the solution was measured by using a liquid chromatography (LC) analysis, and the results were shown in below Table 1.

On the other hand, when the solution containing the ethylbenzene is subjected to the purity analysis as in Example 1, Comparative Examples 2 and 3, the weight ratio of all the components is obtained in terms of wt % based on the total weight of the filtered solution to be analyzed, on the contrary, when the purity in Example 2, Comparative Example 1 and Reference Example 1 is analyzed, the weight ratio of all the components is obtained in terms of wt % based on the total weight of the solid components to be analyzed. Therefore, in Example 1, Comparative Examples 2 and 3, 'wt %' of each solid component dissolved in the solution based on the total weight of the solid components dissolved in the solution obtained by deducting the weight of the ethylbenzene solvent from the filtered solution was calculated and shown in order to directly compare the above Examples, Comparative Examples and Reference Example.

TABLE 1

| wt % | Example 1 | Example 2 | Comparative Example 1 | Comparative Example 2 | Comparative Example 3 | Reference Example 1 |
|---|---|---|---|---|---|---|
| MAH + MA | 0.87 | 0.71 | 1.86 | 1.49 | 1.24 | 0.00 |
| FA | 0.03 | 0.03 | 0.37 | 0.06 | 0.27 | 0.10 |
| PMA | 0.4 | 0.08 | 1.76 | 0.69 | 1.51 | 0.65 |
| PMI | 88.19 | 98.13 | 78.24 | 68.60 | 71.46 | 98.82 |
| PPMA | 0.39 | 0 | 0.76 | 6.74 | 4.79 | 0.00 |
| PPFA | 0.08 | 0 | 0.16 | 1.01 | 0.76 | 0.00 |
| APSI | 0.3 | 0 | 0.45 | 2.20 | 1.84 | 0.00 |
| Others | 9.74 | 1.06 | 16.39 | 19.20 | 18.14 | 0.43 |

As shown in Table 1, from Comparative Example 1 in which the N-phenyl maleimide was synthesized and only distillation was carried out after separating the catalyst without performing washing with water or cooling, it was confirmed that the FA was contained in an excess amount of 0.37 wt %.

From Example 1 in which the cooling to 50° C. and filtering out processes were carried out after separating the catalyst, it was confirmed that most of the FA was removed to 0.03 wt % as compared with Comparative Example 1. This is because the FA solubility in the organic solvent (ethylbenzene) at the above temperature is low, and the FA is precipitated and removed as a solid. In addition, it was confirmed that the removal effect of the FA through the above cooling process was equal to or better than that of Reference Example 1 in which impurities were removed through performing washing with water.

On the other hand, as the content of the FA was not changed in Example 2 in which the distillation was further carried out in addition to Example 1, it was confirmed that the FA was difficult to remove through distillation. This is because the FA has a similar boiling point to the N-phenyl maleimide, and the FA is difficult to remove even through distillation.

However, as the cooling temperature of 30° C. in Comparative Example 2, it was confirmed that there was no significant difference in the removal efficiency of the FA, but the content of the PMI was decreased when it was cooled to the excessively low temperature. This is because even the N-phenyl maleimide was precipitated as a solid and lost.

In addition, as the cooling temperature of 80° C. in Comparative Example 3, it was confirmed that the removal efficiency of the FA was not excellent when it was not cooled to the cooling temperature of the present invention. The cause seems that the FA solubility in the organic solvent was not sufficiently lowered, so that the FA was partially precipitated as a solid, and thus all of the FA could not be removed through filtration.

The above description for the present invention is illustratively provided, and it can be thus understood that a person skilled in the art to which the present invention pertains could easily modify the present invention into another specific form without changing the technical idea or essential features. Therefore, the examples described above are merely illustrative in all the aspects and should be construed as not being limited to the examples set forth herein.

The invention claimed is:

1. A method for purifying N-substituted maleimide, comprising:
 1) a step of preparing an N-substituted maleimide solution by reacting with maleic anhydride and a primary amine in the presence of an organic solvent and a catalyst; and
 2) a step of cooling the N-substituted maleimide solution to 50° C. to 60° C. to precipitate a solidified organic acid, removing the solidified organic acid by filtering.

2. The method for purifying the N-substituted maleimide of claim 1, wherein the organic solvent is at least one selected from the group consisting of benzene, toluene, xylene, o-xylene, ethylbenzene, isopropylbenzene, cumene, mesitylene, tert-butylbenzene, pseudocumene, trimethylhexane, octane, tetrachloroethane, nonane, chlorobenzene, ethylcyclohexane, m-dichlorobenzene, sec-butylbenzene, p-dichlorobenzene, decane, p-cymene, o-dichlorobenzene, butylbenzene, decahydronaphthalene, tetrahydronaphthalene, dodecane, naphthalene and cyclohexylbenzene.

3. The method for purifying the N-substituted maleimide of claim 1, wherein the organic acid is at least one selected from the group consisting of fumaric acid (FA), maleic acid (MA), N-phenyl maleamic acid (PMA), N-phenyl maleimide (PMI), N-(2,5-dioxo-1-phenyl-3-pyrrolidinyl)-N-phenyl maleamic acid) (PPMA), N-(2,5-dioxo-1-phenyl-3-pyrrolidinyl)-N-phenyl fumaranilic acid) (PPFA) and 2-anilino-N-phenyl succinimide (APSI).

4. The method for purifying the N-substituted maleimide of claim 1, wherein a boiling point of the organic acid is no more than 30° C. lower and no more than 40° C. higher than a boiling point of the N-substituted maleimide.

5. The method for purifying the N-substituted maleimide of claim 1, wherein an amount of the organic acid contained in the N-substituted maleimide solution of step 1) is 0.1 wt % to 5.0 wt %.

6. The method for purifying the N-substituted maleimide of claim 1, wherein an amount of the organic acid contained in the N-substituted maleimide solution after carrying out step 2) is 0.03 wt % to 0.1 wt %.

7. The method for purifying the N-substituted maleimide of claim 1, further comprising a step of separating a catalyst from the N-substituted maleimide solution, and the separating the catalyst is carried out through the filtering in step 2), or through high-temperature filtration at 100° C. to 140° C. before carrying out step 2).

8. The method for purifying the N-substituted maleimide of claim 1, wherein the catalyst is a zirconium (IV) hydrogen phosphate $(Zr(H_2PO_4)_2)$ solid-acid-catalyst.

9. The method for purifying the N-substituted maleimide of claim 1, further comprising a step of distilling the N-substituted maleimide solution after carrying out step 2).

10. The method for purifying the N-substituted maleimide of claim 1, wherein a water washing process is not carried out.

11. The method for purifying the N-substituted maleimide of claim 1, wherein the primary amine is at least one selected from the group consisting of methylamine, ethylamine, n-propylamine, iso-propylamine, n-butylamine, sec-butylamine, iso-butylamine, tert-butylamine, n-hexylamine, n-octylamine, n-decylamine, n-dodecylamine, cyclohexylamine, and aniline.

12. The method for purifying the N-substituted maleimide of claim 1, wherein the N-substituted maleimide is at least one selected from the group consisting of: N-alkyl maleimide such as N-methyl maleimide, N-ethyl maleimide, N-hexyl maleimide, N-octyl maleimide, or N-dodecyl maleimide; N-benzyl maleimide; N-cycloalkyl maleimide such as N-cyclohexyl maleimide; N-phenyl maleimide; and N-substituted phenyl maleimide, in which a phenyl group is substituted with a nitro group, an alkoxy group, an alkyl group, a carboxyl group, a hydroxyl group, or a halogen group, such as N-nitrophenyl maleimide, N-methoxyphenyl maleimide, N-methylphenyl maleimide, N-carboxyphenyl maleimide, N-hydroxyphenyl maleimide, N-chlorophenyl maleimide, N-dimethylphenyl maleimide, N-dichlorophenyl maleimide, N-bromophenyl maleimide, N-dibromophenyl maleimide, N-trichlorophenyl maleimide, or N-tribromophenyl maleimide.

* * * * *